US011298006B2

(12) United States Patent
Kobayashi et al.

(10) Patent No.: US 11,298,006 B2
(45) Date of Patent: Apr. 12, 2022

(54) MEDICAL IMAGING APPARATUS AND MEDICAL OBSERVATION SYSTEM

(71) Applicant: SONY OLYMPUS MEDICAL SOLUTIONS INC., Tokyo (JP)

(72) Inventors: Motoaki Kobayashi, Tokyo (JP); Kohtaro Amano, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 280 days.

(21) Appl. No.: 16/335,689

(22) PCT Filed: Jun. 27, 2017

(86) PCT No.: PCT/JP2017/023485
§ 371 (c)(1),
(2) Date: Mar. 22, 2019

(87) PCT Pub. No.: WO2018/066185
PCT Pub. Date: Apr. 12, 2018

(65) Prior Publication Data
US 2019/0307314 A1 Oct. 10, 2019

(30) Foreign Application Priority Data
Oct. 7, 2016 (JP) .............................. JP2016-198752

(51) Int. Cl.
*A61B 1/00* (2006.01)
*A61B 1/04* (2006.01)
(Continued)

(52) U.S. Cl.
CPC ............ *A61B 1/0019* (2013.01); *A61B 1/002* (2013.01); *A61B 1/00105* (2013.01);
(Continued)

(58) Field of Classification Search
CPC ............ A61B 1/00105; A61B 1/00186; A61B 1/00193; A61B 1/0019; A61B 1/002;
(Continued)

(56) References Cited

U.S. PATENT DOCUMENTS 4,364,629 A * 12/1982 Lang ................... A61B 1/00193
359/377
5,522,789 A * 6/1996 Takahashi .......... G02B 23/2415
600/166

(Continued)

FOREIGN PATENT DOCUMENTS

| CN | 105549193 A | 5/2016 |
| JP | 06-059199 | 3/1994 |

(Continued)

OTHER PUBLICATIONS

Extended European Search Report dated Aug. 21, 2019 in European Application No. 17858025.4-1124.

(Continued)

*Primary Examiner* — Aaron B Fairchild
*Assistant Examiner* — Shankar Raj Ghimire
(74) *Attorney, Agent, or Firm* — Xsensus LLP

(57) ABSTRACT

A medical imaging apparatus 11 captures observation light from an observed region inside a subject. This medical imaging apparatus 11 includes plural types of optical path separation devices 5, 6 which respectively guide first observation light and second observation light that are included in observation light from scopes 2, 3 that are inserted into the subject, take in the observation light from the observed region inside the subject, and emit the observation light, along optical paths being different from each other; and an imaging apparatus 7 which is shared by the plural types of optical path separation devices 5,6, is detachably connected to the plural types of optical path separation devices 5,6, and (Continued)

captures the first observation light and the second observation light respectively guided by the connected optical path separation devices.

15 Claims, 8 Drawing Sheets

(51) Int. Cl.
*G02B 23/24* (2006.01)
*A61B 1/002* (2006.01)
*H04N 13/204* (2018.01)
*A61B 1/06* (2006.01)

(52) U.S. Cl.
CPC ...... *A61B 1/00186* (2013.01); *A61B 1/00193* (2013.01); *A61B 1/043* (2013.01); *G02B 23/24* (2013.01); *G02B 23/2415* (2013.01); *A61B 1/042* (2013.01); *A61B 1/0661* (2013.01); *H04N 13/204* (2018.05)

(58) Field of Classification Search
CPC ....... A61B 1/042; A61B 1/043; A61B 1/0661; G02B 23/24; G02B 23/2415; H04N 13/204
See application file for complete search history.

(56) References Cited

U.S. PATENT DOCUMENTS

| | | | | |
|---|---|---|---|---|
| 5,577,991 A * | 11/1996 | Akui | ................... | A61B 1/0005 600/111 |
| 5,588,948 A * | 12/1996 | Takahashi | ............... | A61B 1/042 600/111 |
| 5,689,365 A * | 11/1997 | Takahashi | ............... | G02B 23/24 359/362 |
| 5,860,912 A * | 1/1999 | Chiba | ................... | H04N 13/15 600/111 |
| 5,865,829 A | 2/1999 | Kitajima | | |
| 5,976,071 A * | 11/1999 | Sekiya | ................... | A61B 1/055 600/111 |
| 6,025,873 A * | 2/2000 | Nishioka | .................. | H04N 7/18 348/72 |
| 6,139,490 A * | 10/2000 | Breidenthal | ............ | A61B 1/002 600/111 |
| 6,191,809 B1 * | 2/2001 | Hori | ..................... | H04N 13/189 348/45 |
| 7,671,888 B2 * | 3/2010 | Nogami | ............. | A61B 1/00193 348/45 |
| 9,192,286 B2 * | 11/2015 | Kazakevich | ......... | H04N 13/239 |
| 2003/0083551 A1 * | 5/2003 | Takahashi | .......... | A61B 1/00193 600/166 |
| 2011/0043612 A1 * | 2/2011 | Keller | .................... | G03B 35/20 348/49 |
| 2011/0228049 A1 * | 9/2011 | Kazakevich | ....... | A61B 1/00009 348/45 |
| 2013/0176395 A1 | 7/2013 | Kazakevich | | |
| 2013/0338439 A1 | 12/2013 | Kosugi et al. | | |
| 2015/0168710 A1 * | 6/2015 | Zobel | ................. | A61B 1/00193 348/45 |

FOREIGN PATENT DOCUMENTS

| | | | | |
|---|---|---|---|---|
| JP | 06-160731 | | 6/1994 | |
| JP | 07-261099 | | 10/1995 | |
| JP | 2007090044 A | | 4/2007 | |
| WO | 96/37796 A1 | | 11/1996 | |
| WO | WO-9637796 A1 * | | 11/1996 | ......... G02B 23/2415 |
| WO | WO-2009117483 A1 * | | 9/2009 | ........... A61B 5/0071 |

OTHER PUBLICATIONS

International Search Report dated Sep. 19, 2017 for PCT/JP2017/023485, filed on Jun. 27, 2017, 7 pages including English Translation.

* cited by examiner

MEDICAL IMAGING APPARATUS AND MEDICAL OBSERVATION SYSTEM

CROSS-REFERENCE TO RELATED APPLICATIONS

The present application is based on PCT filing PCT/JP2017/023485, filed Jun. 27, 2017, which claims priority to JP 2016-198752, filed Oct. 7, 2016, the entire contents of which are incorporated herein by reference.

TECHNICAL FIELD

The present invention relates to a medical imaging apparatus that captures observation light from an observed region inside a subject and a medical observation system.

BACKGROUND ART

In the past, in a medical field, an endoscope apparatus which captures a subject (the inside of a living body) by using an imaging element and is used to three-dimensionally observe the inside of the living body has been known (for example, see Patent Literatures 1 and 2).

In the endoscope apparatus (the three-dimensional endoscope apparatus) described in Patent Literature 1, a twin lens relay type is employed as a three-dimensional observation type (hereinafter, 3D type). Specifically, in the endoscope apparatus, a pair of optical systems having the same configuration is provided in parallel inside a scope (a rigid endoscope) and the pair of optical systems respectively takes in first observation light and second observation light having parallax. Then, the first observation light and the second observation light are respectively captured by an imaging apparatus (TV camera (charge coupled device (CCD))).

Further, in an endoscope apparatus (a three-dimensional rigid endoscope) described in Patent Literature 2, a single lens pupil split type is employed as a 3D type. Specifically, in the endoscope apparatus, an optical system is disposed in one optical path inside a scope (an insertion part), observation light is taken by the optical system, and the observation light is separated into two regions to generate first observation light and second observation light having parallax. Then, the first observation light and the second observation light are respectively captured by an imaging apparatus (CCD).

CITATION LIST

Patent Literature

Patent Literature 1: JP H06-160731 A
Patent Literature 2: JP H06-59199 A

DISCLOSURE OF INVENTION

Technical Problem

Incidentally, in the twin lens relay type, since the optical systems taking the first observation light and the second observation light are separately disposed, there is a merit that sufficient parallax can be obtained and the inside of the living body can be stereoscopically viewed with a sufficient stereoscopic effect. In contrast, in the twin lens relay type, there is a demerit that an image rotation cannot be handled in the case of using a perspective type scope having a viewing field diagonally forward with respect to the center axis of the scope. Specifically, since the first observation light and the second observation light taken by the pair of optical systems are respectively captured by a pair of CCDs, it is not possible to rotate the scope about the center axis of the scope with respect to the imaging apparatus for the purpose of observing observed regions at various positions. Further, when all of the scope and the imaging apparatus are rotated about the center axis of the scope, an image displayed on a display screen is also rotated with the rotation.

Meanwhile, in the single lens pupil split type, since the observation light is taken by the optical system disposed in one optical path and the observation light is separated into two regions, the problem of the above-described twin lens relay type does not arise even when the optical system is rotated about the center axis of the scope. That is, in the single lens pupil split type, there is a merit that an image rotation can be handled. In contrast, in the single lens pupil split type, since the observation light taken by the optical system disposed in one optical path is separated into two regions to generate the first observation light and the second observation light, there is a demerit that sufficient parallax cannot be obtained and a stereoscopic effect will be diluted.

Then, when any 3D type of the twin lens relay type and the single lens pupil split type can be selected according to a technique in consideration of the above-described merits and demerits, convenience can be improved. However, in order to improve the convenience, for example, a user who needs both the endoscope apparatus dedicated to the twin lens relay type described in Patent Literature 1 and the endoscope apparatus dedicated to the single lens pupil split type described in Patent Literature 2 separately purchases them. As a result, there is a first problem that a cost (a purchase cost and a maintenance cost) taken for the purchase or maintenance increases and a sufficient storage space needs to be secured.

Further, when viewed from a manufacturer side, if each of the endoscope apparatus dedicated to the twin lens relay type described in Patent Literature 1 and the endoscope apparatus dedicated to the single lens pupil split type described in Patent Literature 2 is manufactured, the number of parts increases and a manufacturing cost increases. As a result, there is a second problem that a product price becomes higher.

The invention has been made in view of the above-described circumstances and a first object of the invention is to provide a medical imaging apparatus and a medical observation system capable of decreasing a purchase cost and a maintenance cost of a user and a storage space and improving convenience. Further, a second object of the invention is to provide a medical imaging apparatus and a medical observation system capable of decreasing a manufacturing cost and improving convenience.

Solution to Problem

In order to solve the above problem and to achieve the object, a medical imaging apparatus according to the present invention is a medical imaging apparatus that captures observation light from an observed region inside a subject, the medical imaging apparatus including: plural types of optical path separation devices which respectively guide first observation light and second observation light that are included in observation light from a scope that is inserted into the subject, takes in the observation light from the observed region inside the subject, and emits the observation light, along optical paths being different from each other; and an imaging apparatus which is shared by the plural types of optical path separation devices, is detachably connected to the plural types of optical path separation devices, and captures the first observation light and the second observation light respectively guided by the connected optical path separation devices.

In the medical imaging apparatus according to the present invention, the scope is configured as a twin lens relay scope in which a first optical system is disposed in a first optical path, a second optical system is disposed in a second optical path parallel to the first optical path, and the first observation light and the second observation light that have parallax are taken in by the first optical system and the second optical system and emitted from the twin lens relay scope, and any one optical path separation device of the plural types of optical path separation devices includes a deflecting unit which deflects the first observation light and the second observation light toward the optical paths being different from each other, in the above invention.

In the medical imaging apparatus according to the present invention, the scope is configured as a single lens scope in which an optical system is disposed in one optical path and the optical system takes in and emits the observation light, and any one optical path separation device of the plural types of optical path separation devices includes a pupil split unit which is disposed at a position of a pupil of the optical system and separates a light flux in the pupil into two regions so that the observation light is separated into the first observation light and the second observation light that have parallax, in the above inventions.

In the medical imaging apparatus according to the present invention, the scope is configured as a single lens scope in which an optical system is disposed in one optical path and the optical system takes in and emits the observation light, and any one optical path separation device of the plural types of optical path separation devices includes a wavelength separating unit which separates the observation light into the first observation light which is infrared light and the second observation light which is visible light, in the above inventions.

In the medical imaging apparatus according to the present invention, the scope is configured as a single lens scope in which an optical system is disposed in one optical path and the optical system takes in and emits the observation light, and any one optical path separation device of the plural types of optical path separation devices includes a beam splitter which reflects a part of the observation light to generate the first observation light and transmits a part of the observation light to generate the second observation light, in the above inventions.

In the medical imaging apparatus according to the present invention, at least one optical path separation device of the plural types of optical path separation devices is detachably connected to the scope.

A medical observation system according to the present invention includes the above-described medical imaging apparatus; and a scope which is inserted into a subject, takes in observation light from the observed region inside the subject, and emits the observation light.

In the medical observation system according to the present invention, plural types of the scopes are provided, and any one of the plural types of the scopes is configured as a twin lens relay scope in which a first optical system is disposed in a first optical path, a second optical system is disposed in a second optical path parallel to the first optical path, and the first observation light and the second observation light having parallax are taken in by the first optical system and the second optical system and are emitted from the twin lens relay scope, in the above invention.

In the medical observation system according to the present invention, plural types of the scopes are provided, and any one of the plural types of the scopes is configured as a single lens scope in which an optical system is disposed in one optical path and the optical system takes in and emits the observation light.

Advantageous Effects of Invention

A medical imaging apparatus according to this invention includes the above-described plural types of optical path separation devices and a single imaging apparatus. For this reason, it is possible to configure the endoscope apparatus according to a technique by connecting a scope such as plural types of (for example, twin lens relay type, single lens pupil split type, or the like) scopes and the single imaging apparatus using any one of plural types of optical path separation devices. That is, the imaging apparatus can be shared when plural types of (for example, the twin lens relay type, single lens pupil split type, or the like) endoscope apparatuses are configured.

Thus, since the imaging apparatus is shared, it is possible to decrease a purchase cost and a maintenance cost of a user in that the user does not need to purchase each of plural types of endoscope apparatuses. Further, since the imaging apparatus is shared as compared with a case in which each of plural types of endoscope apparatuses is accommodated, it is possible to decrease the type of device to be accommodated and a storage space. That is, according to the medical imaging apparatus of the invention, there is an effect that a purchase cost and a maintenance cost of a user and a storage space can be decreased and convenience is improved.

Further, when viewed from a manufacturer side, since the imaging apparatus is shared, it is possible to decrease the number of parts and to decrease a manufacturing cost in that each of plural types of endoscope apparatuses does not need to be manufactured. That is, according to the medical imaging apparatus of the invention, there is an effect of decreasing a manufacturing cost and improving convenience. Further, since it is possible to decrease a product price by decreasing a manufacturing cost, there is an effect of decreasing a user's purchase cost.

Since the medical observation system according to the invention includes the above-described medical imaging apparatus, the same effects as those of the above-described medical imaging apparatus are obtained.

MODE(S) FOR CARRYING OUT THE INVENTION

Figure 1:
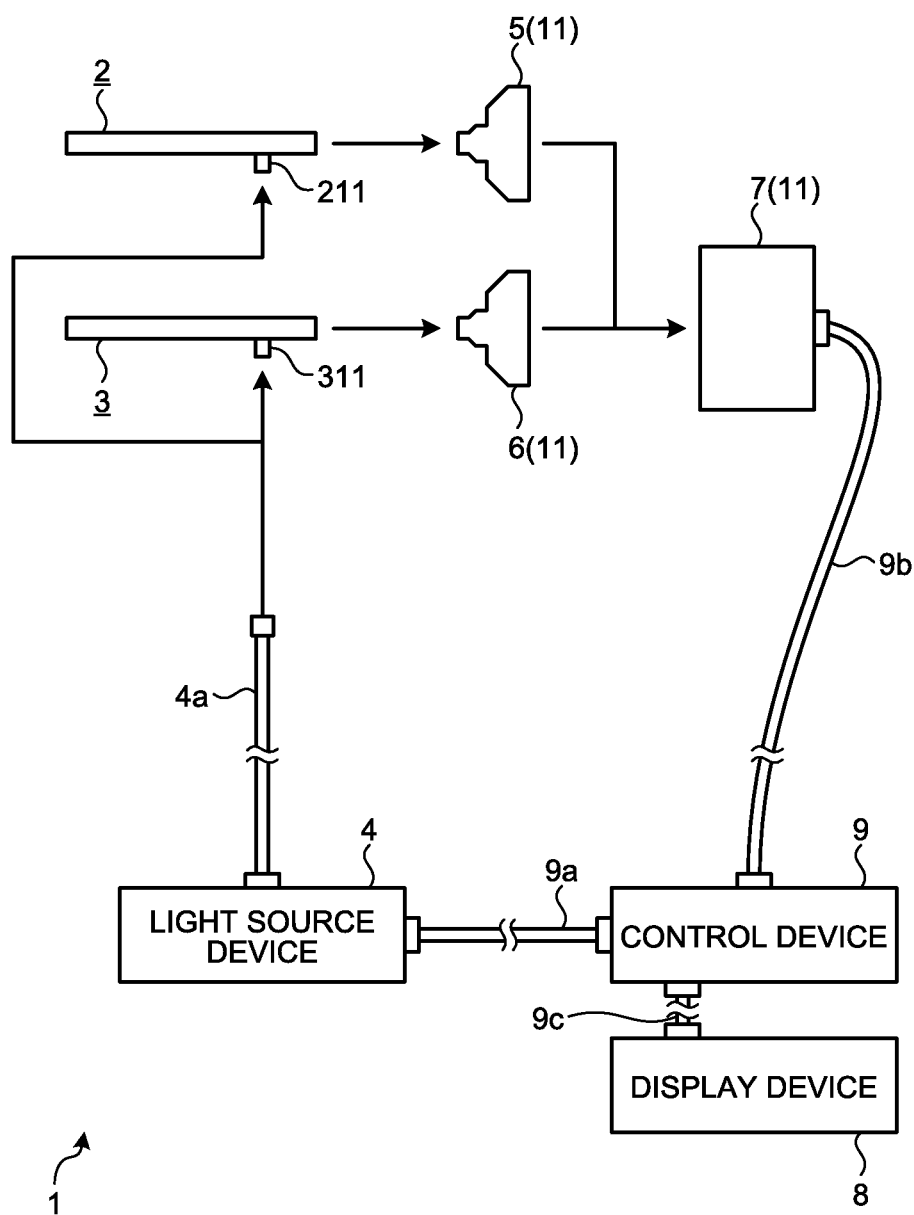
FIG. 1 is a diagram illustrating a schematic configuration of a medical observation system according to a first embodiment.

Hereinafter, a mode for carrying out the invention (hereinafter, embodiments) will be described with reference to the drawings. Incidentally, the invention is not limited to the embodiments to be described below. Additionally, in the description of the drawings, the same reference numerals are given to the same parts.

First Embodiment

[Schematic Configuration of Medical Observation System]

FIG. 1 is a diagram illustrating a schematic configuration of a medical observation system 1 according to a first embodiment.

The medical observation system 1 is a system which is used in a medical field to three-dimensionally observe the inside of a living body and is configured to change a 3D type according to a technique. In the first embodiment, the medical observation system 1 is configured to change the 3D type to either one of a twin lens relay type (see FIG. 2) and a single lens pupil split type (see FIG. 3).

The medical observation system 1 includes, as illustrated in FIG. 1, a twin lens relay scope 2, a single lens scope 3, a light source device 4, a light guide cable 4a, two types of first and second optical path separation devices 5 and 6, a camera head 7, a display device 8, a control device 9, and first to third transmission cables 9a to 9c.

Incidentally, in the medical observation system 1, when the 3D type is the twin lens relay type, the twin lens relay scope 2, the light source device 4, the light guide cable 4a, the first optical path separation device 5, the camera head 7, the display device 8, the control device 9, and the first to third transmission cables 9a to 9c are used. Meanwhile, when the 3D type is the single lens pupil split type, the single lens scope 3, the light source device 4, the light guide cable 4a, the second optical path separation device 6, the camera head 7, the display device 8, the control device 9, and the first to third transmission cables 9a to 9c are used.

That is, the twin lens relay scope 2 and the first optical path separation device 5 are configurations dedicated to the twin lens relay type. Further, the single lens scope 3 and the second optical path separation device 6 are configurations dedicated to the single lens pupil split type. Then, the light source device 4, the light guide cable 4a, the camera head 7, the display device 8, the control device 9, and the first to third transmission cables 9a to 9c are configurations shared by the twin lens relay type and the single lens pupil split type.

The twin lens relay scope 2, which is inserted into a living body, takes in first observation light and second observation light having parallax from an observed region inside the living body and to emit the first observation light and the second observation light.

The single lens scope 3, which is inserted into a living body, takes in observation light from an observed region inside the living body and to emit the observation light.

Then, the twin lens relay scope 2 and the single lens scope 3 function as a scope according to the invention. Incidentally, detailed configurations of the twin lens relay scope 2 and the single lens scope 3 will be described later.

The light source device 4, to which one end of the light guide cable 4a is connected, supplies light for illuminating the inside of the living body to the one end of the light guide cable 4a under the control of the control device 9.

While the one end of the light guide cable 4a is connected to the light source device 4, the other end thereof is connected to the twin lens relay scope 2 or the single lens scope 3. Then, the light guide cable 4a supplies the light supplied from the light source device 4 to the twin lens relay scope 2 or the single lens scope 3.

The first optical path separation device 5 is detachably connected to the twin lens relay scope 2 and guides the first observation light and the second observation light, which are emitted from the twin lens relay scope 2, along optical paths different from each other.

The second optical path separation device 6 is detachably connected to the single lens scope 3 and separates the observation light, which is emitted from the single lens scope 3, into third observation light (corresponding to first observation light according to the invention) and fourth observation light (corresponding to second observation light according to the invention) having parallax, which are then guided along optical paths different from each other.

Here, the first and second optical path separation devices 5 and 6 function as an optical path separation device according to the invention. Incidentally, detailed configurations of the first and second optical path separation devices 5 and 6 will be described later.

The camera head 7 is detachably connected to each of the first and second optical path separation devices 5 and 6. Then, when the 3D type is the twin lens relay type, the camera head 7 captures the first observation light guided by the first optical path separation device 5 to generate a right eye image signal and captures the second observation light guided by the first optical path separation device 5 to generate a left eye image signal. Meanwhile, when the 3D type is the single lens pupil split type, the camera head 7 captures the third observation light guided by the second optical path separation device 6 to generate a right eye image signal and captures the fourth observation light guided by the second optical path separation device 6 to generate a left eye image signal.

Then, the camera head 7 functions as an imaging apparatus according to the invention. Incidentally, a detailed configuration of the camera head 7 will be described later.

The display device 8 is configured by using, for example, a 3D display of an integral imaging type or a multi-eye type and displays a three-dimensional image based on a three-dimensional video signal processed by the control device 9.

The control device 9 is configured to include a central processing unit (CPU) and the like and is connected to the light source device 4, the camera head 7, and the display device 8 through the first to third transmission cables 9a to 9c, respectively. Then, the control device 9 outputs a control signal to the light source device 4 through the first transmission cable 9a and comprehensively control the operation of the light source device 4. Further, the control device 9 applies various image processes onto the left and right eye image signals received from the camera head 7 through the second transmission cable 9b, and thus generates and outputs a three-dimensional video signal to the display device 8 through the third transmission cable 9c. Further, the control device 9 outputs a control signal, a synchronization signal, a clock, and electric power to the camera head 7 through the second transmission cable 9b.

Incidentally, as to the transmission of the left and right eye image signals from the camera head 7 to the control device 9 through the second transmission cable 9b, the left and right eye image signals may be transmitted by optical signals or transmitted by electric signals. The same applies to the transmission of the control signal, the synchronization signal, and the clock from the control device 9 to the camera head 7 through the second transmission cable 9b.

[Configuration Dedicated to Twin Lens Relay Type]

Next, the twin lens relay scope 2 and the first optical path separation device 5 which are configurations dedicated to the twin lens relay type will be described.

Figure 2:
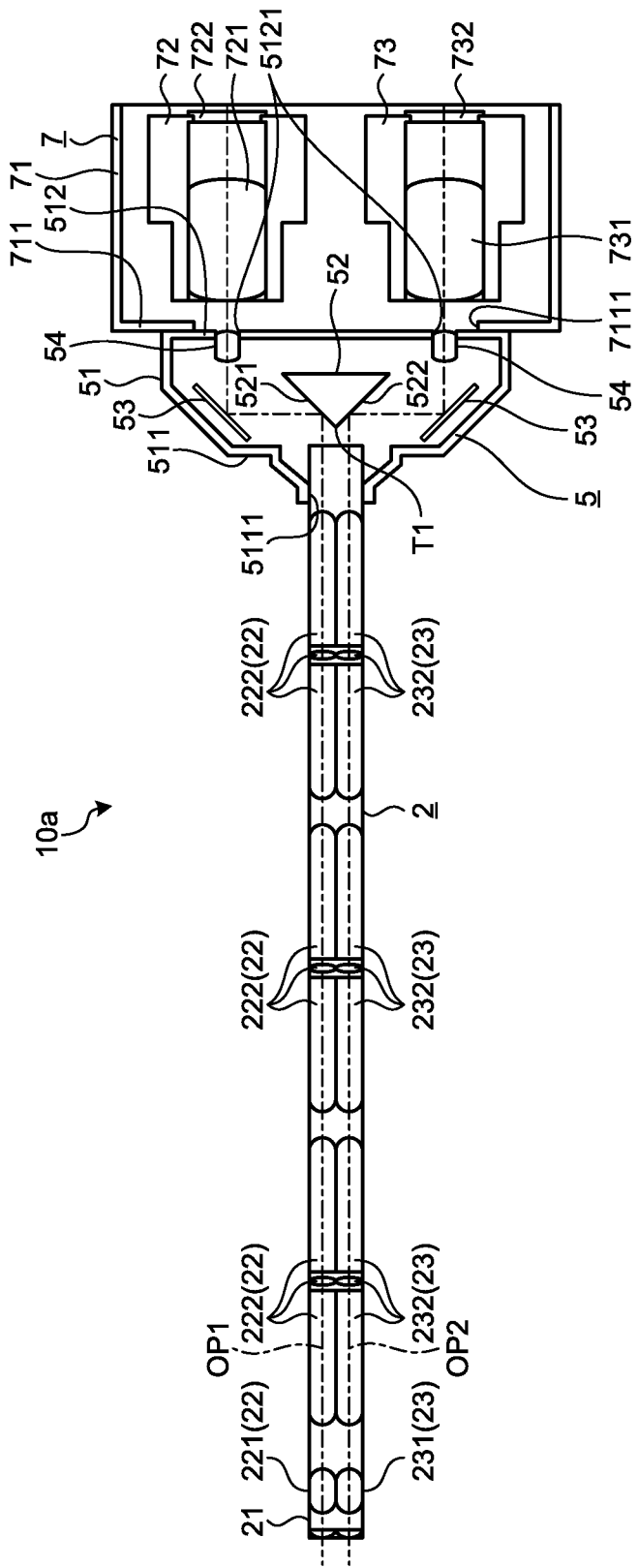
FIG. 2 is a diagram illustrating a case in which the medical observation system illustrated in FIG. 1 is used in a twin lens relay type and is a diagram illustrating a state in which a twin lens relay scope, a first optical path separation device, and a camera head are assembled.

FIG. 2 is a diagram illustrating a case in which the medical observation system 1 is used in the twin lens relay type and is a diagram illustrating a state in which the twin lens relay scope 2, the first optical path separation device 5, and the camera head 7 are assembled.

The twin lens relay scope 2 includes, as illustrated in FIG. 2, an insertion tube 21 and first and second optical systems 22 and 23.

The insertion tube 21 is rigid or at least partially flexible and has an elongated shape.

Inside the insertion tube 21, first and second optical paths OP1 and OP2 (FIG. 2) are set which extend along the center axis of the insertion tube 21 and are juxtaposed with each other to be symmetrical (vertically symmetrical in FIG. 2) with respect to the center axis.

Further, the outer peripheral surface of the insertion tube 21 is provided with a connection connector 211 (FIG. 1) which protrudes in the radial direction and is connected to the other end of the light guide cable 4a. Incidentally, the connection connector 211 is not illustrated in FIG. 2 for convenience of description. The light supplied from the light source device 4 to the twin lens relay scope 2 through the light guide cable 4a is emitted from a distal end of the insertion tube 21 (a left end portion of FIG. 2) through a light guide (illustration omitted) provided inside the insertion tube 21 and is emitted into the living body. Then, the observation light (the first observation light and the second observation light) irradiated into the living body and then reflected from the observed region inside the living body is taken in from the distal end of the insertion tube 21.

The first optical system 22 is disposed in the first optical path OP1 inside the insertion tube 21 and includes a first objective optical system 221 and a first relay optical system 222 in order from the distal end side. The first objective optical system 221 is provided at the distal end of the insertion tube 21 and takes in the first observation light from the observed region inside the living body.

The first relay optical system 222 guides the first observation light taken in at the first objective optical system 221 to a proximal end of the insertion tube 21 (a left end portion of FIG. 2). Then, the first observation light is emitted from the proximal end of the insertion tube 21.

The second optical system 23 is disposed in the second optical path OP2 inside the insertion tube 21 and includes a second objective optical system 231 and a second relay optical system 232 in order from the distal end side.

The second objective optical system 231 is provided at the distal end of the insertion tube 21 and takes in the second observation light from the observed region inside the living body.

The second relay optical system 232 guides the second observation light taken in at the second objective optical system 231 to the proximal end of the insertion tube 21. Then, the second observation light is emitted from the proximal end of the insertion tube 21.

As described above, the first and second optical systems 22 and 23 are disposed inside the insertion tube 21 with a predetermined gap interposed therebetween in the radial direction. For this reason, the first observation light and the second observation light having parallax are taken in and emitted by the twin lens relay scope 2.

The first optical path separation device 5 functions as an adapter which connects the twin lens relay scope 2 and the camera head 7 to each other. The first optical path separation device 5 includes, as illustrated in FIG. 2, a casing 51, a triangular prism 52, a pair of mirrors 53, and a pair of eyepiece optical systems 54.

The casing 51 has a substantially rectangular parallelepiped shape and accommodates respective members 52 to 54.

In this casing 51, an insertion port 5111 which protrudes outward and into which the proximal end side of the insertion tube 21 is inserted is formed on one side surface 511.

Further, in the casing 51, a pair of communication holes 5121 is formed in the vertical direction (the radial direction of the insertion tube 21) with a predetermined gap interposed therebetween in FIG. 2 on a side surface 512 facing the side surface 511 so as to be symmetrical with respect to the center axis of the insertion tube 21 thereby to communicate the inside with the outside.

Moreover, a connection portion (illustration omitted) to be mechanically connected to the camera head 7 is provided on the outer surface of the casing 51.

The triangular prism 52 is formed as a triangular prism of which a bottom surface has a right-angled isosceles triangle shape. Further, the triangular prism 52 is disposed inside the casing 51 in a posture in which the center axis of the insertion tube 21 passes through an apex T1 of the right-angled isosceles triangle serving as the bottom surface and is orthogonal to a hypotenuse, while the axis of the triangular prism is orthogonal to the drawing paper of FIG. 2 and the insertion tube 21 is inserted into the insertion port 5111.

Then, the triangular prism 52 reflects the first observation light emitted from the twin lens relay scope 2 upward in FIG. 2 by a first side surface 521 constituting one of two sides having the apex T1 of the right-angled isosceles triangle serving as the bottom surface interposed therebetween. Further, the triangular prism 52 reflects the second observation light emitted from the twin lens relay scope 2 downward in FIG. 2 by a second side surface 522 constituting the other of the two sides. For these reasons, the first observation light and the second observation light respectively travel in the opposite directions of 180° in the radial direction of the insertion tube 21 (the vertical direction in FIG. 2) through the triangular prism 52.

That is, the triangular prism 52 deflects the first observation light and the second observation light to optical paths different from each other, and functions as a deflector according to the invention.

The pair of mirrors 53 is disposed inside the casing 51 with a predetermined gap interposed therebetween in the vertical direction of FIG. 2 to be symmetrical with respect to the center axis of the insertion tube 21. Then, the first observation light and the second observation light from the triangular prism 52 are reflected by the pair of mirrors 53 and respectively travel in a direction parallel to the center axis of the insertion tube 21.

The pair of eyepiece optical systems 54 is disposed inside the casing 51 with a predetermined gap interposed therebetween in the vertical direction in FIG. 2 to be symmetrical with respect to the center axis of the insertion tube 21. Then, the pair of eyepiece optical systems 54 emits the first observation light and the second observation light from the pair of mirrors 53 to the outside through the pair of communication holes 5121.

[Configuration Dedicated to Single Lens Pupil Split Type]

Next, the single lens scope 3 and the second optical path separation device 6 which are configurations dedicated to the single lens pupil split type will be described.

Figure 3:
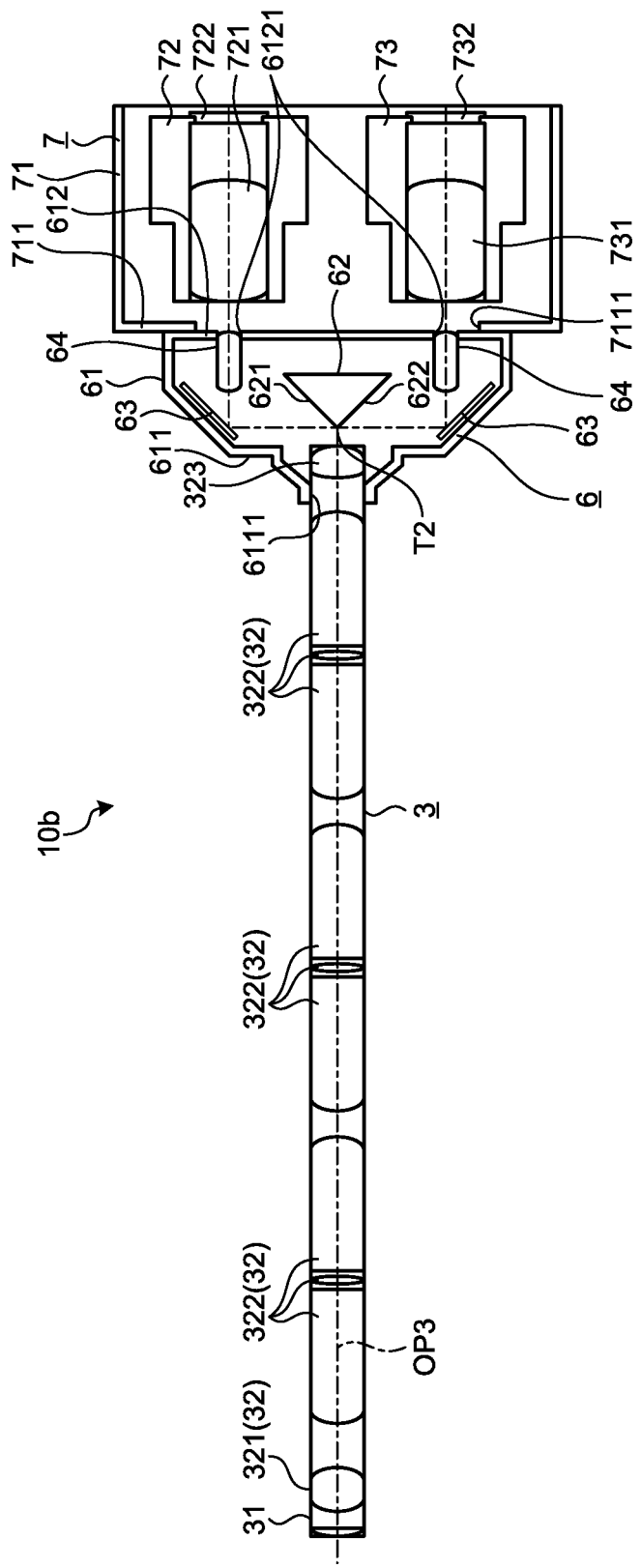
FIG. 3 is a diagram illustrating a case in which the medical observation system illustrated in FIG. 1 is used in a single lens pupil split type and is a diagram illustrating a state in which a single lens scope, a second optical path separation device, and a camera head are assembled.

FIG. 3 is a diagram illustrating a case in which the medical observation system 1 is used in the single lens pupil split type and is a diagram illustrating a state in which the single lens scope 3, the second optical path separation device 6, and the camera head 7 are assembled.

The single lens scope 3 includes, as illustrated in FIG. 3, an insertion tube 31 and an optical system 32.

The insertion tube 31 is rigid or at least partially flexible and has an elongated shape.

Inside the insertion tube 31, one optical path OP3 is set on the center axis of the insertion tube 31.

Further, the outer peripheral surface of the insertion tube 31 is provided with a connection connector 311 (FIG. 1) which protrudes in the radial direction and is connected to the other end of the light guide cable 4a. Incidentally, the connection connector 311 is not illustrated in FIG. 3 for convenience of description. The light supplied from the light source device 4 to the single lens scope 3 through the light guide cable 4a is emitted from the distal end of the insertion tube 31 (a left end portion of FIG. 3) through a light guide (illustration omitted) provided inside the insertion tube 31 and is irradiated into the living body. Then, the observation light irradiated into the living body and then reflected from the observed region inside the living body is taken in from the distal end of the insertion tube 31.

The optical system 32 is disposed in the optical path OP3 inside the insertion tube 31 and includes an objective optical system 321, a relay optical system 322, and an eyepiece optical system 323 in order from the distal end side.

The objective optical system 321 is provided at the distal end of the insertion tube 31 and takes the observation light from the observed region inside the living body.

The relay optical system 322 guides the observation light taken by the objective optical system 321 to the proximal end of the insertion tube 31 (the right end portion of FIG. 3).

The eyepiece optical system 323 is provided at the proximal end of the insertion tube 31 and emits the observation light guided by the relay optical system 322 from the proximal end of the insertion tube 31.

The second optical path separation device 6 functions as an adapter which connects the single lens scope 3 and the camera head 7 to each other. The second optical path separation device 6 includes, as illustrated in FIG. 3, a casing 61, a triangular prism 62, a pair of mirrors 63, and a pair of relay optical systems 64.

The casing 61 has a substantially rectangular parallelepiped shape and accommodates respective members 62 to 64.

In this casing 61, an insertion port 6111 which protrudes outward and into which the proximal end side of the insertion tube 31 is inserted is formed on one side surface 611.

Further, in the casing 61, a pair of communication holes 6121 is formed in the vertical direction (the radial direction of the insertion tube 31) with a predetermined gap interposed therebetween in FIG. 3 on a side surface 612 facing the side surface 611 so as to be symmetrical with respect to the center axis of the insertion tube 31 thereby to communicate the inside with the outside. Incidentally, the separation dimension between the pair of communication holes 6121 is set to be the same as the separation dimension between the pair of communication holes 5121.

Moreover, a connection portion (illustration omitted) to be mechanically connected to the camera head 7 is provided on the outer surface of the casing 61.

The triangular prism 62 is formed as a triangular prism of which a bottom surface has a right-angled isosceles triangle shape. Further, the triangular prism 62 is disposed inside the casing 61 in a posture in which the center axis of the insertion tube 31 passes through an apex T2 of the right-angled isosceles triangle serving as the bottom surface and is orthogonal to a hypotenuse, while the axis of the triangular prism is orthogonal to the drawing paper of FIG. 3 and the insertion tube 31 is inserted into the insertion port 6111. Further, the apex T2 of the right-angled isosceles triangle serving as the bottom surface of the triangular prism 62 coincides with the pupil position of the optical system 32.

Then, the triangular prism 62 reflects the third observation light, which is one half region of the observation light emitted from the single lens scope 3, upward in FIG. 3 by a first side surface 621 constituting one of two sides interposing the apex T2 of the right-angled isosceles triangle serving as the bottom surface. Further, the triangular prism 62 reflects the fourth observation light, which is the other half region of the observation light emitted from the single lens scope 3, downward in FIG. 3 by a second side surface 622 constituting the other of the two sides. For these reasons, the third observation light and the fourth observation light respectively travel in the opposite directions of 180° in the radial direction of the insertion tube 31 (the vertical direction in FIG. 3) through the triangular prism 62.

That is, the triangular prism 62 separates the observation light into the third observation light and the fourth observation light having parallax by separating the light flux in the pupil of the optical system 32 into two regions and functions as a pupil separation unit according to the invention.

The pair of mirrors 63 is disposed inside the casing 61 with a predetermined gap interposed therebetween in the vertical direction of FIG. 3 to be symmetrical with respect to the center axis of the insertion tube 31. Then, the third observation light and the fourth observation light from the triangular prism 62 are reflected by the pair of mirrors 63 and respectively travel in a direction parallel to the center axis of the insertion tube 31.

The pair of relay optical systems 64 is disposed inside the casing 61 with a predetermined gap interposed therebetween in the vertical direction of FIG. 3 to be symmetrical with respect to the center axis of the insertion tube 31. Then, the pair of relay optical systems 64 emits the third observation light and the fourth observation light from the pair of mirrors 63 to the outside through the pair of communication holes 6121.

[Configuration of Camera Head Shared by Twin Lens Relay Type and Single Lens Pupil Split Type]

Next, a configuration of the camera head 7 which is shared by the twin lens relay type and the single lens pupil split type will be described with reference to FIG. 2 and FIG. 3.

The camera head 7 includes, as illustrated in FIG. 2 or FIG. 3, a casing 71 and first and second imaging units 72 and 73.

The casing 71 has a substantially rectangular parallelepiped shape and accommodates first and second imaging units 72 and 73.

In this casing 71, a communication hole 7111 communicating the inside with the outside is formed on one side surface 711.

Further, a connection portion (illustration omitted) to be mechanically connected to the first optical path separation device 5 or the second optical path separation device 6 is provided on the outer surface of the casing 71.

The first imaging unit 72 is disposed at a position facing the eyepiece optical system 54 or the relay optical system 64 located at the upper side in FIG. 2 or 3 in a state in which the first optical path separation device 5 or the second optical path separation device 6 is attached to the camera head 7 inside the casing 71.

Then, the first imaging unit 72 generates a right eye image signal by capturing the first observation light that is emitted from the eyepiece optical system 54 located at the upper side and passes through the communication holes 5121 and 7111 or the third observation light that is emitted from the relay optical system 64 located at the upper side and passes through the communication holes 6121 and 7111.

The first imaging unit 72 includes, as illustrated in FIG. 2 or 3, a first imaging optical system 721 and a first imaging element 722.

The first imaging optical system 721 is configured by using one or a plurality of lenses movable along the optical axis and forms an image of the first observation light or the third observation light on an imaging surface of the first imaging element 722.

The first imaging optical system 721 is provided with an optical zoom mechanism (illumination omitted) changing a viewing angle or a focus mechanism (illumination omitted) changing a focus by moving one or a plurality of lenses. Then, the control device 9 operates the optical zoom mechanism or the focus mechanism by outputting a control signal to the camera head 7 through the second transmission cable 9b and changes the viewing angle or the focus of the first imaging optical system 721.

The first imaging element 722 generates a right eye image signal by capturing the first observation light or the third observation light under the control of the control device 9.

The first imaging element 722 is configured by using a sensor chip in which an imaging element (illustration omitted) such as a CCD or a CMOS (complementary metal oxide semiconductor) receiving the first observation light or the third observation light formed as an image by the first imaging optical system 721 and converting the light into an electric signal is integrated with a signal processing unit (illumination omitted) performing a signal process (A/D conversion or the like) on the electric signal (analog signal) from the imaging element and outputting a right eye image signal. Incidentally, the above-described signal processing unit may not be integrally formed with the above-described imaging element and may be separated therefrom.

The second imaging unit 73 is disposed at a position facing the eyepiece optical system 54 or the relay optical system 64 located at the lower side in FIG. 2 or 3 in a state in which the first optical path separation device 5 or the second optical path separation device 6 is attached to the camera head 7 inside the casing 71.

Then, the second imaging unit 73 generates a left eye image signal by capturing the second observation light that is emitted from the eyepiece optical system 54 located at the lower side and passes through the communication holes 5121 and 7111 or the fourth observation light that is emitted from the relay optical system 64 located at the lower side and passes through the communication holes 6121 and 7111.

The second imaging unit 73 includes, as illustrated in FIG. 2 or 3, a second imaging optical system 731 and a second imaging element 732.

The second imaging optical system 731 has the same configuration as that of the first imaging optical system 721 and forms an image of the second observation light or the fourth observation light on an imaging surface of the second imaging element 732.

The second imaging element 732 has the same configuration as that of the first imaging element 722 and generates a left eye image signal by capturing the second observation light or the fourth observation light under the control of the control device 9.

Here, the first and second optical path separation devices 5 and 6 and the camera head 7 correspond to a medical imaging apparatus 11 (FIG. 1) according to the invention. Further, hereinafter, for convenience of description, the twin lens relay scope 2, the first optical path separation device 5 and the camera head 7 will be referred to as an endoscope apparatus 10a (FIG. 2), and the single lens scope 3, the second optical path separation device 6, and the camera head 7 will be referred to as an endoscope apparatus 10b (FIG. 3).

According to the above-described first embodiment, the following effects are obtained.

The medical imaging apparatus 11 according to the first embodiment includes two types of first and second optical path separation devices 5 and 6 and the single camera head 7. For this reason, it is possible to configure the endoscope apparatuses 10a and 10b according to a technique by connecting the twin lens relay scope 2 or the single lens scope 3 to the camera head 7 using either one of the first and second optical path separation devices 5 and 6. That is, the camera head 7 can be shared when the twin lens relay type and single lens pupil split type endoscope apparatuses 10a and 10b are configured.

Thus, since the camera head 7 is shared, it is possible to decrease a purchase cost and a maintenance cost of a user in that the user does not need to purchase each of the twin lens relay type and single lens pupil split type endoscope apparatuses. Further, since the camera head 7 is shared as compared with a case in which each of the twin lens relay type and single lens pupil split type endoscope apparatuses is stored, it is possible to decrease the types of devices to be stored and to decrease a storage space. That is, according to the medical imaging apparatus 11 of the first embodiment, there is an effect that a purchase cost and a maintenance cost of a user and a storage space can be decreased and convenience is improved.

Further, when viewed from a manufacturer side, since the camera head 7 is shared, it is possible to decrease the number of parts and to decrease a manufacturing cost in that each of the twin lens relay type endoscope apparatus and the single lens pupil split type endoscope apparatus does not need to be manufactured. That is, according to the medical imaging apparatus 11 of the first embodiment, there is an effect of decreasing a manufacturing cost and improving convenience. Further, since it is possible to decrease a product price by decreasing a manufacturing cost, there is an effect of decreasing a user's purchase cost.

Second Embodiment

Next, a second embodiment of the invention will be described.

In the description below, the same reference numerals will be given to the same components as those of the above-described first embodiment and a detailed description thereof will be omitted or simplified.

Figure 4:
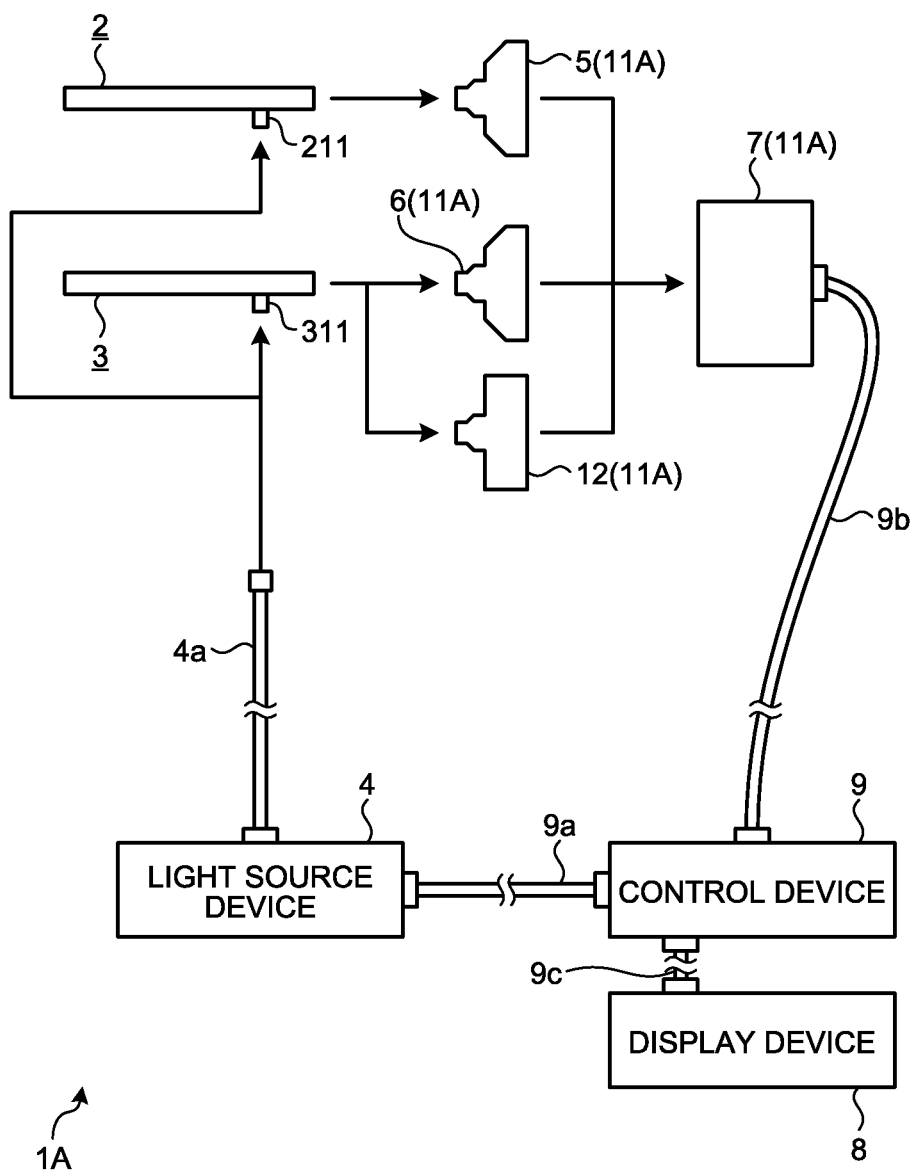
FIG. 4 is a diagram illustrating a schematic configuration of a medical observation system according to a second embodiment.

FIG. 4 is a diagram illustrating a schematic configuration of a medical observation system 1A according to the second embodiment.

The medical observation system 1A according to the second embodiment is configured to be modifiable to an infrared observation type, which is not the 3D type, in addition to the modifiability of the 3D type to either one of the twin lens relay type and the single lens pupil split type. Specifically, in the medical observation system 1A, a third optical path separation device 12 is added to the medical observation system 1 (FIG. 1) described in the above-described first embodiment as illustrated in FIG. 4.

Furthermore, in the medical observation system 1A, the single lens scope 3, the light source device 4, the light guide cable 4a, the third optical path separation device 12, the camera head 7, the display device 8, and the control device 9 are used when the infrared observation is performed.

Figure 5:
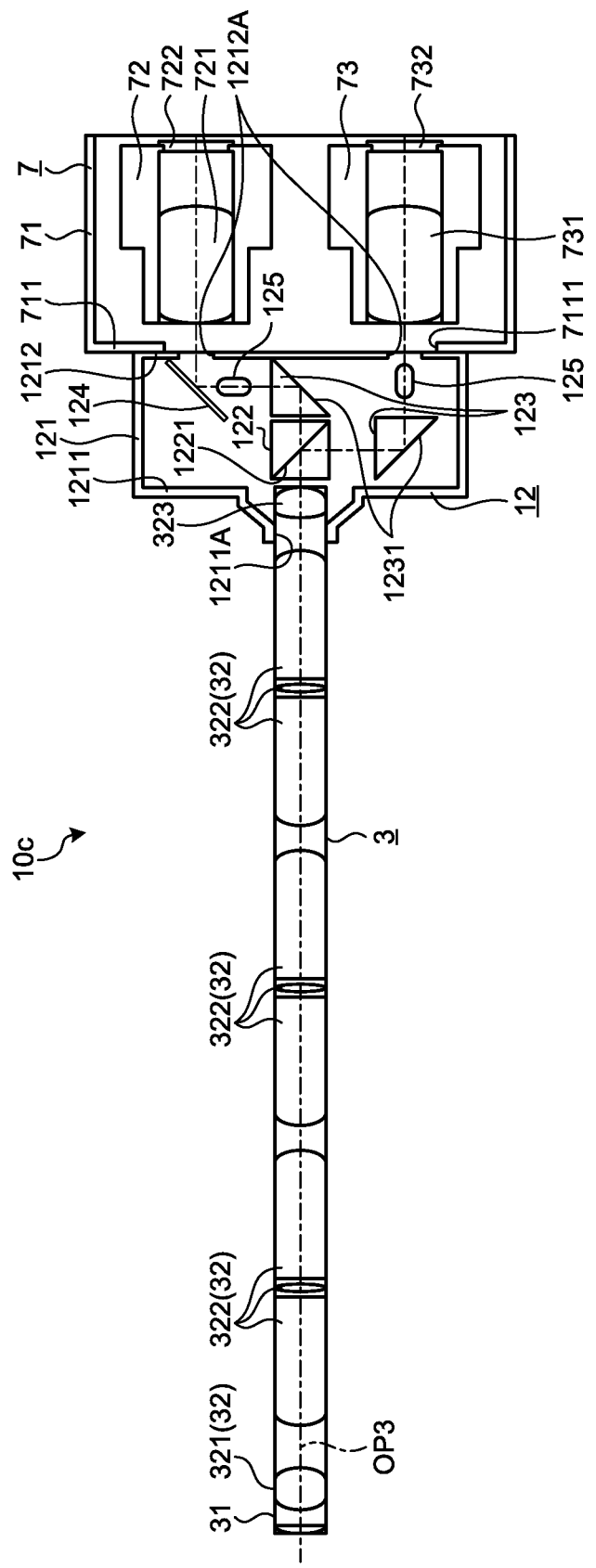
FIG. 5 is a diagram illustrating a case in which the medical observation system illustrated in FIG. 4 is used in an infrared observation and is a diagram illustrating a state in which a single lens scope, a third optical path separation device, and a camera head are assembled.

FIG. 5 is a diagram illustrating a case in which the medical observation system 1A is used for the infrared observation and is a diagram illustrating a state in which the single lens scope 3, the third optical path separation device 12, and the camera head 7 are assembled.

The third optical path separation device 12 is detachably connected to each of the single lens scope 3 and the camera head 7 and is configured to separate the observation light emitted from the single lens scope 3 into fifth observation light (corresponding to the first observation light according to the invention) corresponding to infrared light and sixth observation light (corresponding to second observation light according to the invention) corresponding to visible light and to respectively guide these bands of light along optical paths different from each other.

Then, the third optical path separation device 12 functions as an optical path separation device according to the invention.

The third optical path separation device 12 functions as an adapter which connects the single lens scope 3 and the camera head 7 to each other similarly to the second optical path separation device 6. Then, the third optical path separation device 12 includes, as illustrated in FIG. 5, a casing 121, an infrared reflection prism 122, a pair of reflection prisms 123, a reflection mirror 124, and a pair of relay optical systems 125.

The casing 121 has a substantially rectangular parallelepiped shape and accommodates respective members 122 to 125.

In this casing 121, an insertion port 1211A which protrudes outward and into which the proximal end side of the insertion tube 31 is inserted is formed on one side surface 1211.

Further, in the casing 121, a pair of communication holes 1212A is formed in the vertical direction (the radial direction of the insertion tube 31) with a predetermined gap interposed therebetween in FIG. 5 on a side surface 1212 facing the side surface 1211 so as to be symmetrical with respect to the center axis of the insertion tube 31 thereby to communicate the inside with the outside. Incidentally, the separation dimension between the pair of communication holes 1212A is set to be the same as the separation dimension between the pair of communication holes 6121.

Moreover, a connection portion (illustration omitted) to be mechanically connected to the camera head 7 is provided on the outer surface of the casing 121.

The infrared reflection prism 122 has a substantially cubic shape into which two triangular prisms of which bottom surfaces each is a right-angled isosceles triangle are combined. Then, the infrared reflection prism 122 is disposed inside the casing 121 in a posture in which the center axis of the insertion tube 31 passes through a center position of a boundary face 1221 of each of the triangular prisms and intersects the boundary face 1221 at 45° while the axis of each of the triangular prisms is orthogonal to the drawing paper of FIG. 5 and the insertion tube 31 is inserted into the insertion port 1211A. Further, the boundary face 1221 is provided with an optical thin film such as a dielectric multilayer film which reflects infrared light and transmits visible light.

Then, the infrared reflection prism 122 reflects the fifth observation light, which is infrared light included in the observation light emitted from the single lens scope 3, downward in FIG. 5 by the boundary face 1221. Further, the infrared reflection prism 122 transmits the sixth observation light, which is visible light included in the observation light emitted from the single lens scope 3, through the boundary face 1221.

That is, the infrared reflection prism 122 separates the observation light into the fifth observation light, which is infrared light, and the sixth observation light, which is visible light, and functions as a wavelength separator according to the invention.

Each of the pair of reflection prisms 123 is formed as a triangular prism of which a bottom surface has a right-angled isosceles triangle shape and is disposed inside the casing 121 in a posture in which the axis of the triangular prism is orthogonal to the drawing paper of FIG. 5.

Then, one reflection prism 123 of the pair of reflection prisms 123 reflects the fifth observation light from the infrared reflection prism 122 by a side surface 1231 constituting a hypotenuse of the right-angled isosceles triangle serving as the bottom surface so that the light travels in a direction parallel to the center axis of the insertion tube 31 to the communication hole 1212A located at the lower side. Further, the other reflection prism 123 reflects the sixth observation light from the infrared reflection prism 122 upward in FIG. 5 by the side surface 1231 constituting a hypotenuse of the right-angled isosceles triangle serving as the bottom surface.

The pair of relay optical systems 125 is respectively disposed at the rear stages of the optical paths of the pair of reflection prisms 123. Then, one relay optical system 125 of the pair of relay optical systems 125 emits the fifth observation light from the above-described one reflection prism 123 to the outside (the second imaging unit 73) through the communication hole 1212A located at the lower side. Further, the other relay optical system 125 is disposed between the above-described other reflection prism 123 and the reflection mirror 124 and guides the sixth observation light from the other reflection prism 123 to the reflection mirror 124.

The reflection mirror 124 reflects the sixth observation light from the above-described other relay optical system 125 so that the light travels in a direction parallel to the center axis of the insertion tube 31 and is emitted to the outside (the first imaging unit 72) through the communication hole 1212A located at the upper side in FIG. 5.

Here, the first to third optical path separation devices 5, 6, and 12 and the camera head 7 correspond to a medical imaging apparatus 11A (FIG. 4) according to the invention. Further, hereinafter, for convenience of description, the single lens scope 3, the third optical path separation device 12, and the camera head 7 will be referred to as an endoscope apparatus 10c (FIG. 5).

According to the above-described second embodiment, the following effects are obtained in addition to the same effects as those of the above-described first embodiment.

The medical imaging apparatus 11A according to the second embodiment further includes a third optical path separation device 12. For this reason, when the single lens scope 3 and the camera head 7 are connected to each other by using the third optical path separation device 12, the infrared observation type endoscope apparatus 10c can be configured in addition to the twin lens relay type or the single lens pupil split type. That is, the camera head 7 can be shared when the twin lens relay type, single lens pupil split type, and infrared observation type endoscope apparatuses 10a to 10c are configured. Further, the single lens scope 3 can be shared when the single lens pupil split type and infrared observation type endoscope apparatuses 10b and 10c are configured.

Thus, since the single lens scope 3 or the camera head 7 is shared, it is possible to decrease a purchase cost and a maintenance cost of a user in that the user does not need to purchase each of the twin lens relay type, single lens pupil split type, and infrared observation type endoscope apparatuses. Further, since the single lens scope 3 and the camera head 7 are shared as compared with a case in which each of the twin lens relay type, single lens pupil split type, and infrared observation type endoscope apparatuses is stored, and it is possible to decrease the types of devices to be accommodated and to decrease a storage space. That is, according to the medical imaging apparatus 11A of the second embodiment, there is an effect that a purchase cost and a maintenance cost of a user and a storage space can be decreased and convenience is improved. Further, when viewed from a manufacturer side, since the single lens scope 3 or the camera head 7 is shared, it is possible to decrease the number of parts and to decrease a manufacturing cost in that each of the twin lens relay type endoscope apparatus, the single lens pupil split type endoscope apparatus, and the infrared observation type endoscope apparatus does not need to be manufactured. That is, according to the medical imaging apparatus 11A of the second embodiment, there is an effect of decreasing a manufacturing cost and improving convenience. Further, since it is possible to decrease a product price by decreasing a manufacturing cost, there is an effect of decreasing a user's purchase cost.

For example, the infrared observation is performed as below.

First, indocyanine green (ICG) is injected into a subject. Then, the control device 9 performs coloring or the like corresponding to luminance intensity on an image signal corresponding to the fifth observation light which is the infrared light output from the second imaging unit 73. Further, the control device 9 overlaps an image subjected to the coloring or the like with respect to an image corresponding to an image signal corresponding to the sixth observation light which is the visible light output from the first imaging unit 72. Accordingly, the dynamics of blood vessels and lymph vessels beneath the tissue surface can be observed non-invasively.

Third Embodiment

Next, a third embodiment of the invention will be described.

In the description below, the same reference numerals will be given to the same components as those of the above-described third embodiment and a detailed description thereof will be omitted or simplified.

Figure 6:
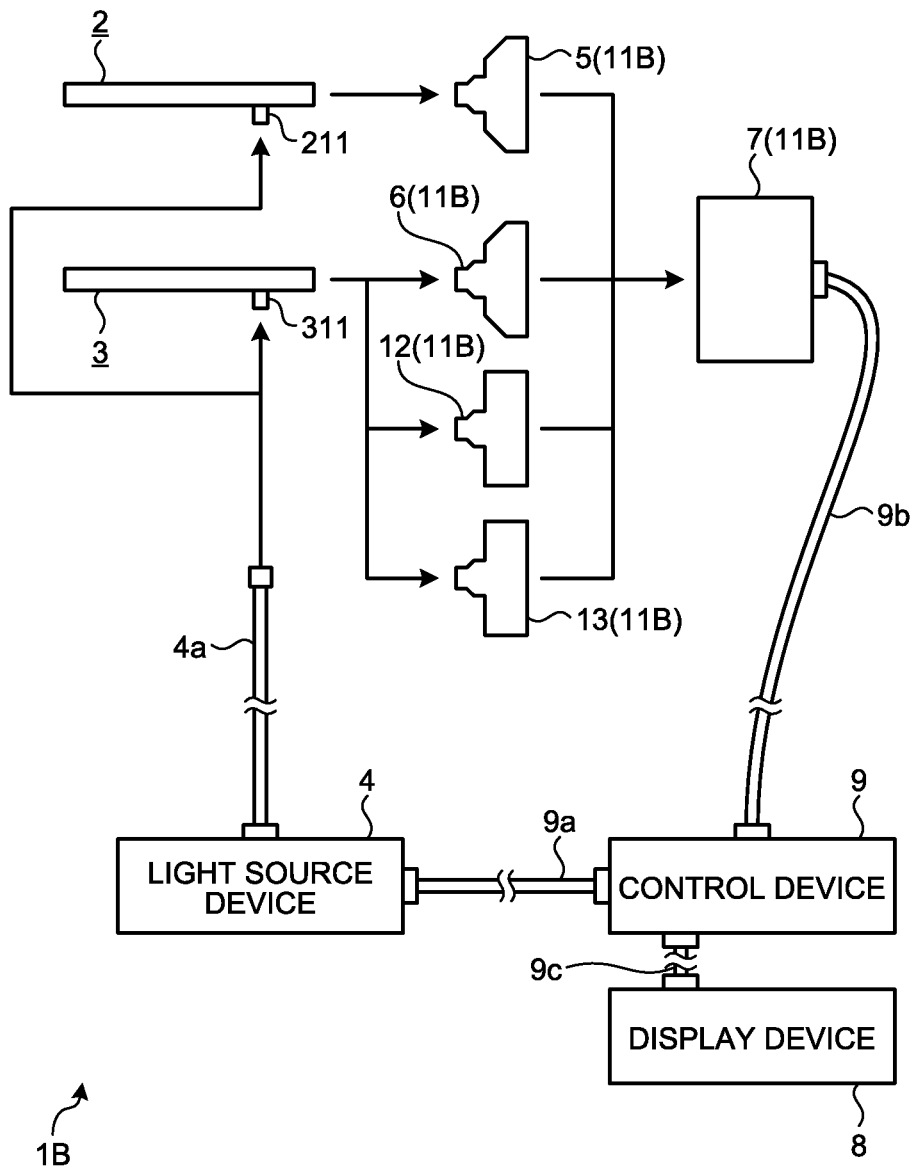
FIG. 6 is a diagram illustrating a schematic configuration of a medical observation system according to a third embodiment.

FIG. 6 is a diagram illustrating a schematic configuration of a medical observation system 1B according to the third embodiment.

The medical observation system 1B according to the third embodiment is configured to be modifiable to a high dynamic range (HDR) observation type, which is not the 3D type, in addition to the modifiability of the 3D type to either one of the twin lens relay type and the single lens pupil split type and the modifiability to the infrared observation type, which is not the 3D type. Specifically, in the medical observation system 1B, as illustrated in FIG. 6, a fourth optical path separation device 13 is added to the medical observation system 1A (FIG. 4) described in the above-described second embodiment.

Furthermore, in the medical observation system 1B, the single lens scope 3, the light source device 4, the light guide cable 4a, the fourth optical path separation device 13, the camera head 7, the display device 8, and the control device 9 are used when the HDR observation is performed.

Figure 7:
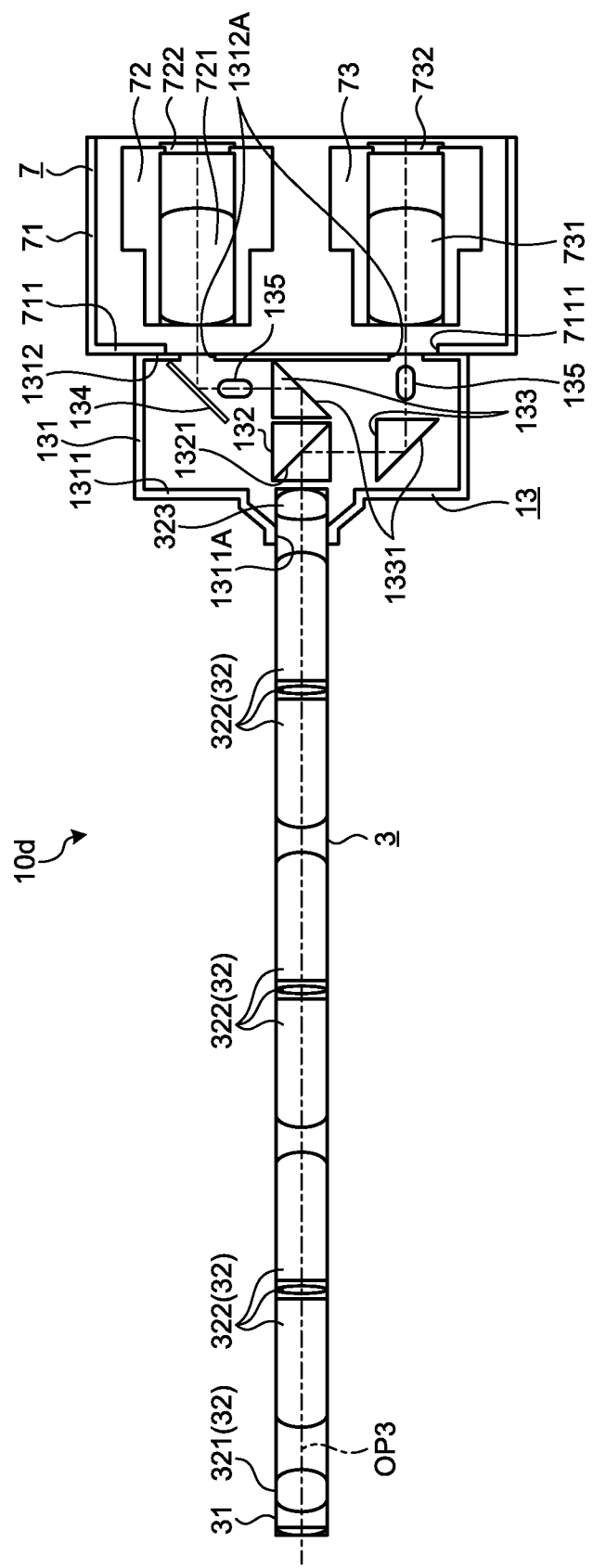
FIG. 7 is a diagram illustrating a case in which the medical observation system illustrated in FIG. 6 is used in an HDR observation and is a diagram illustrating a state in which a single lens scope, a fourth optical path separation device, and a camera head are assembled.

FIG. 7 is a diagram illustrating a case in which the medical observation system 1B is used for the HDR observation and is a diagram illustrating a state in which the single lens scope 3, the fourth optical path separation device 13, and the camera head 7 are assembled.

The fourth optical path separation device 13 is detachably connected to the single lens scope 3 and the camera head 7 and is configured to separate the observation light emitted from the single lens scope 3 into seventh observation light (corresponding to the first observation light according to the invention) and eighth observation light (corresponding to the second observation light according to the invention) and to guide these bands of light along optical paths different from each other.

Then, the fourth optical path separation device 13 functions as an optical path separation device according to the invention.

The fourth optical path separation device 13 functions as an adapter which connects the single lens scope 3 and the camera head 7 to each other similarly to the third optical path separation device 12. Then, the fourth optical path separation device 13 includes, as illustrated in FIG. 7, a casing 131, a beam splitter 132, a pair of reflection prisms 133, a reflection mirror 134, and a pair of relay optical systems 135.

The casing 131 has a substantially rectangular parallelepiped shape and accommodates respective members 132 to 135.

In this casing 131, an insertion port 1311A which protrudes outward and into which the proximal end side of the insertion tube 31 is inserted is formed on one side surface 1311.

Further, in the casing 131, a pair of communication holes 1312A is formed in the vertical direction (the radial direction of the insertion tube 31) with a predetermined gap interposed therebetween in FIG. 7 on a side surface 1312 facing the side surface 1311 so as to be symmetrical with respect to the center axis of the insertion tube 31 thereby to communicate the inside with the outside. Furthermore, the separation dimension between the pair of communication holes 1312A is set to be the same as the separation dimension between the pair of communication holes 1212A.

Moreover, a connection portion (illustration omitted) to be mechanically connected to the camera head 7 is provided on the outer surface of the casing 131.

The beam splitter 132 has a substantially cubic shape into which two triangular prisms of which bottom surfaces each is a right-angled isosceles triangle are combined. Then, the beam splitter 132 is disposed inside the casing 131 in a posture in which the center axis of the insertion tube 31 passes through a center position of a boundary face 1321 of each of the triangular prisms and intersects the boundary face 1321 at 45° while the axis of each of the triangular prisms is orthogonal to the drawing paper of FIG. 7 and the insertion tube 31 is inserted into the insertion port 1311A. Further, the boundary face 1321 is provided with an optical thin film such as a dielectric multilayer film which sets, for example, a light amount ratio between transmitted light and reflected light of 80%:20%.

Then, the beam splitter 132 reflects a part of the observation light emitted from the single lens scope 3 by the boundary face 1321 thereby to generate the seventh observation light, and transmits a part of the observation light emitted from the single lens scope 3 through the boundary face 1321 thereby to generate the eighth observation light.

Each of the pair of reflection prisms 133 is formed as a triangular prism of which a bottom surface has a right-angled isosceles triangle shape and is disposed inside the casing 131 in a posture in which the axis of the triangular prism intersects the drawing paper of FIG. 7.

Then, one reflection prism 133 of the pair of reflection prisms 133 reflects the seventh observation light from the beam splitter 132 by a side surface 1331 constituting a hypotenuse of the right-angled isosceles triangle, which is the bottom surface, so that the light travels in a direction parallel to the center axis of the insertion tube 31 to the communication hole 1312A located at the lower side. Further, the other reflection prism 133 reflects the eighth observation light from the beam splitter 132 upward in FIG. 7 by the side surface 1331 constituting a hypotenuse of the right-angled isosceles triangle, which is the bottom surface.

The pair of relay optical systems 135 is respectively disposed at the rear stages of the optical paths of the pair of reflection prisms 133. Then, one relay optical system 135 of the pair of relay optical systems 135 emits the seventh observation light from the above-described one reflection prism 133 to the outside (the second imaging unit 73) through the communication hole 1312A located at the lower side. Further, the other relay optical system 135 is disposed between the above-described other reflection prism 133 and the reflection mirror 134 and guides the eighth observation light from the other reflection prism 133 to the reflection mirror 134.

The reflection mirror 134 reflects the eighth observation light from the above-described other relay optical system 135 so that the light travels in a direction parallel to the center axis of the insertion tube 31 and is emitted to the outside (the first imaging unit 72) through the communication hole 1312A located at the upper side in FIG. 7.

Here, the first to fourth optical path separation devices 5, 6, 12, and 13 and the camera head 7 correspond to a medical imaging apparatus 11B (FIG. 6) according to the invention. Further, hereinafter, for convenience of description, the single lens scope 3, the fourth optical path separation device 13, and the camera head 7 will be referred to as an endoscope apparatus 10d (FIG. 7).

According to the above-described third embodiment, the following effects are obtained in addition to the same effects as those of the above-described second embodiment.

The medical imaging apparatus 11B according to the third embodiment further includes the fourth optical path separation device 13. For this reason, when the single lens scope 3 and the camera head 7 are connected to each other by using the fourth optical path separation device 13, the HDR observation type endoscope apparatus 10d can be configured in addition to the twin lens relay type, single lens pupil split type, and infrared observation type. That is, the camera head 7 can be shared when the twin lens relay type, single lens pupil split type, infrared observation type, and HDR observation type endoscope apparatuses 10a to 10d are configured. Further, the single lens scope 3 can be shared when the single lens pupil split type, infrared observation type, and HDR observation type endoscope apparatuses 10b to 10d are configured.

Thus, since the single lens scope 3 or the camera head 7 is shared, it is possible to decrease a purchase cost and a maintenance cost of a user in that the user does not need to purchase each of the twin lens relay type, single lens pupil split type, infrared observation type, and HDR observation type endoscope apparatuses. Further, since the single lens scope 3 and the camera head 7 are shared as compared with a case in which each of the twin lens relay type, single lens pupil split type, infrared observation type, and HDR observation type endoscope apparatuses is stored, it is possible to decrease the types of devices to be stored and to decrease a storage space. That is, according to the medical imaging apparatus 11B of the third embodiment, there is an effect that a purchase cost and a maintenance cost of a user and a storage space can be decreased and convenience is improved.

Further, when viewed from a manufacturer side, since the single lens scope 3 or the camera head 7 is shared, it is possible to decrease the number of parts and to decrease a manufacturing cost in that each of the twin lens relay type, single lens pupil split type, infrared observation type, and HDR observation type endoscope apparatuses does not need to be manufactured. That is, according to the medical imaging apparatus 11B of the third embodiment, there is an effect of decreasing a manufacturing cost and improving convenience. Further, since it is possible to decrease a product price by decreasing a manufacturing cost, there is an effect of decreasing a user's purchase cost.

Figure 8:
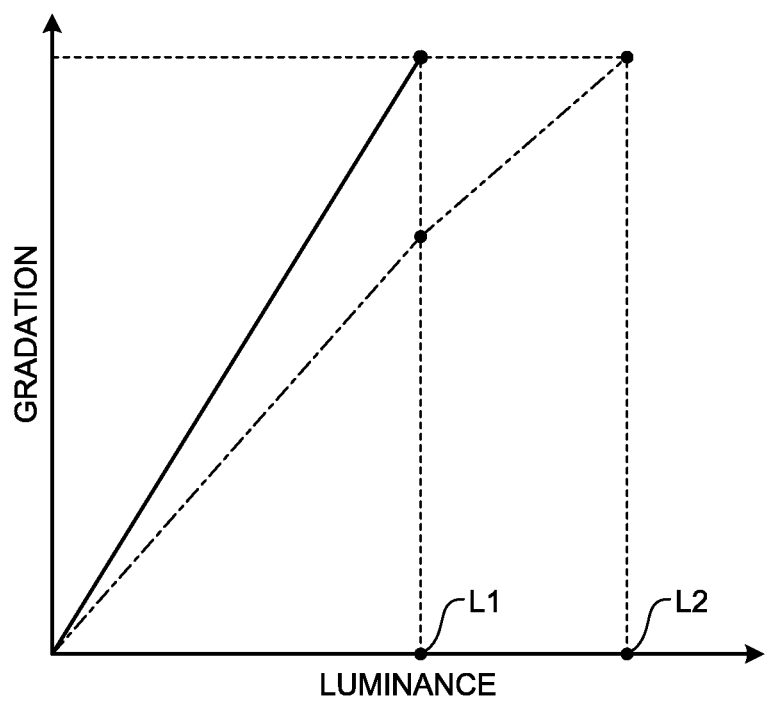
FIG. 8 is a diagram illustrating an HDR observation effect according to the third embodiment.

FIG. 8 is a diagram illustrating an effect of an HDR observation according to the third embodiment.

For example, when the observation light to be separated into the seventh observation light and the eighth observation light by the beam splitter 132 is captured by one imaging element, there is a possibility that blown out highlights occurs (gradation on the high luminance side (luminance L1 or more) is lost) in some cases as indicated by a solid line of FIG. 8.

In the third embodiment, the observation light emitted from the single lens scope 3 is separated into, for example, the seventh observation light of a light amount of 20% and the eighth observation light of a light amount of 80% by the beam splitter 132. For this reason, it is possible to generate and display an image with gradation up to a higher luminance as compared with the case of capturing the light by one imaging element (a solid line of FIG. 8) by allocating gradation (a one-dotted chain line of FIG. 8) at the low luminance side (luminance 0 to L1) to an image signal corresponding to the eighth observation light output from the first imaging unit 72 and allocating gradation (a two-dotted chain line of FIG. 8) at the high luminance side (luminance L1 to L2) to an image signal corresponding to the seventh observation light output from the second imaging unit 73.

Other Embodiments

A mode for carrying out the invention has been described so far, but the invention is not limited to the above-described first to third embodiments.

In the above-described first to third embodiments, the twin lens relay scope 2 and the first optical path separation device 5 are provided attachably/detachably, but the invention is not limited thereto. These components may be integrated with each other. Incidentally, the following configuration is desirable when the twin lens relay scope 2 and the first optical path separation device 5 are configured attachably/detachably as in the above-described first to third embodiments.

For example, when plural types of twin lens relay scope s having different diameters (having a different separation dimension between the first and second optical paths OP1 and OP2) are prepared as the twin lens relay scope 2, the positions of the pair of mirrors 53 are changeable in order to share the first optical path separation device 5 in the plural types of twin lens relay scope s.

In the above-described first to third embodiments, two or more optical path separation devices of the first to fourth optical path separation devices 5, 6, 12, and 13 and the camera head 7 may be referred to as the medical imaging apparatus according to the invention. For example, the second to fourth optical path separation devices 6, 12, and 13 and the camera head 7 may be referred to as the medical imaging apparatus according to the invention. In this case, the single lens scope 3, the second to fourth optical path separation devices 6, 12, and 13, and the camera head 7 correspond to the medical observation system according to the invention.

In the above-described first to third embodiments, the twin lens relay scope 2 and the single lens scope 3 may be configured as a perspective type scope having a viewing field diagonally forward with respect to the center axis of the scope.

In the above-described first to third embodiments, the deflecting unit (the triangular prism 52), the pupil separation unit (the triangular prism 62), the wavelength separating unit (the infrared reflection prism 122), and the beam splitter 132 according to the invention are not limited to the configurations described in the above-described first to third embodiments and other configurations such as a mirror may be employed.

REFERENCE SIGNS LIST 1, 1A, 1B MEDICAL OBSERVATION SYSTEM
2 TWIN LENS RELAY SCOPE
3 SINGLE LENS SCOPE
4 LIGHT SOURCE DEVICE
4a LIGHT GUIDE CABLE
5, 6, 12, 13 FIRST TO FOURTH OPTICAL PATH SEPARATION DEVICES
7 CAMERA HEAD
8 DISPLAY DEVICE
9 CONTROL DEVICE
9a to 9c FIRST TO THIRD TRANSMISSION CABLES
10a to 10d ENDOSCOPE APPARATUS
11, 11A, 11B MEDICAL IMAGING APPARATUS
21, 31 INSERTION TUBE
22, 23 FIRST AND SECOND OPTICAL SYSTEMS
32 OPTICAL SYSTEM
51, 61, 121, 131 CASING
52, 62 TRIANGULAR PRISM
53, 63 MIRROR
54 EYEPIECE OPTICAL SYSTEM
64 RELAY OPTICAL SYSTEM
71 CASING
72, 73 FIRST AND SECOND IMAGING UNITS
122 INFRARED REFLECTION PRISM
123, 133 REFLECTION PRISM
124, 134 REFLECTION MIRROR
125, 135 RELAY OPTICAL SYSTEM
132 BEAM SPLITTER
211, 311 CONNECTION CONNECTOR
221, 231 FIRST AND SECOND OBJECTIVE OPTICAL SYSTEMS
222, 232 FIRST AND SECOND RELAY OPTICAL SYSTEMS
321 OBJECTIVE OPTICAL SYSTEM
322 RELAY OPTICAL SYSTEM
323 EYEPIECE OPTICAL SYSTEM
511, 512, 611, 612, 1211, 1212, 1311, 1312 SIDE SURFACE
521, 621 FIRST SIDE SURFACE
522, 622 SECOND SIDE SURFACE
711 SIDE SURFACE
721, 731 FIRST AND SECOND IMAGING OPTICAL SYSTEMS
722, 732 FIRST AND SECOND IMAGING ELEMENTS
1221, 1321 BOUNDARY FACE
1231, 1331 SIDE SURFACE
5111, 6111, 1211A, 1311A INSERTION PORT
5121, 6121, 1212A, 1312A COMMUNICATION HOLE
7111 COMMUNICATION HOLE
OP1, OP2 FIRST AND SECOND OPTICAL PATHS
OP3 OPTICAL PATH
T1, T2 APEX

The invention claimed is:

1. A medical imaging apparatus that captures observation light from an observed region inside a subject, comprising:
    first optical path separation optics and second optical path separation optics that are different from each other, each of which respectively guide first observation light and second observation light included in observation light from a single lens scope or a twin lens relay scope that is inserted into the subject, receives the observation light from the observed region inside the subject, and transmits the first observation light and the second observation light along optical paths that are different from each other; and
    a camera head to be used with a plurality of optical path separation optics including the first optical path separation optics and the second optical path separation optics and is detachably connected to one of the plurality of optical path separation optics at a time, and captures the first observation light and the second observation light respectively guided by currently connected optical path separation optics.

2. The medical imaging apparatus according to claim 1, on condition that the twin lens relay scope in which a first optical system is disposed in a first optical relay path, a second optical system is disposed in a second optical relay path parallel to the first optical relay path, and the first observation light and the second observation light that have parallax are incident on the first optical system and the second optical system and transmitted from the twin lens relay scope is connected to the camera head, and the second optical path separation optics includes a deflector which deflects the first observation light and the second observation light toward the optical paths that are different from each other.

3. The medical imaging apparatus according to claim 1, wherein the plurality of optical path separation optics further includes a third optical path separation optics that includes a pupil split optics at a position of a pupil of the optical system, wherein the pupil split optics separates a light flux in the pupil into two regions so that the observation light is separated into the first observation light and the second observation light that have parallax, and wherein, on condition that the single lens scope is connected to the camera head, the third optical path separation optics is detachably connected to the camera head.

4. The medical imaging apparatus according to claim 1, wherein the plurality of optical path separation optics further includes:

third optical path separation optics that includes wavelength separating optics that separates the observation light into the first observation light of a first wavelength and the second observation light of a second wavelength, different from the first wavelength.

5. The medical imaging apparatus according to claim 4, wherein the first observation light is infrared light and the second observation light is visible light.

6. The medical imaging apparatus according to claim 1, wherein the plurality of optical path separation optics further includes a fourth optical path separation optics that includes a beam splitter which reflects a part of the observation light to generate the first observation light and transmits a part of the observation light to generate the second observation light, and on condition that the single lens scope is connected to the camera head, the fourth optical path separation optics is detachably connected to the fourth optical path separation optics.

7. The medical imaging apparatus according to claim 1, wherein the first and second optical path separation optics are detachably connected to the single lens scope or the twin lens relay scope, respectively.

8. A medical observation system comprising:
the medical imaging apparatus according to claim 1; and
a scope which is inserted into a subject, receives observation light from the observed region inside the subject, and transmits the observation light.

9. The medical observation system according to claim 8, wherein the twin lens relay scope includes a first optical system in a first relay optical path, a second optical system in a second relay optical path parallel to the first relay optical path, and the first observation light and the second observation light having parallax are received by the first optical system and the second optical system and are transmitted from the twin lens relay scope.

10. The medical observation system according to claim 8, wherein the single lens scope includes an optical system in one optical path, and the optical system and transmits the observation light.

11. A kit for use in medical imaging from an observed region inside a subject, the kit comprising:

first optical path separation optics for use with a single lens scope, the first optical path separation optics to guide first observation light and second observation light included in observation light from the single lens scope that is inserted into the subject along optical paths that are different from each other, receive observation light from the observed region inside the subject, and transmits the first observation light and the second observation light along optical paths that are different from each other; and second optical path separation optics, different from the first optical path separation optics, the second optical path separation optics to guide first observation light and second observation light included in observation light from a twin lens relay scope that is inserted into the subject, receive the observation light from the observed region inside the subject, and transmit the first observation light and the second observation light along optical paths that are different from each other; and a camera head to be used with either at least one of the first optical path separation optics and second optical path separation optics, is detachably connected to at least one of the first and second optical path separation optics at a time, and captures the first observation light and the second observation light respectively guided by currently connected optical path separation optics.

12. The kit according to claim 11, wherein the first observation light is infrared light and the second observation light is visible light.

13. The kit according to claim 11, wherein the second optical path separation optics includes a deflector which deflects the first observation light and the second observation light toward the optical paths that are different from each other.

14. The kit according to claim 11, wherein the plurality of optical path separation optics further includes a third optical path separation optics for use with the camera head and the single lens scope, wherein the third optical path separation optics includes a pupil split optics at a position of a pupil of the optical system that separates a light flux in the pupil into two regions so that the observation light is separated into the first observation light and the second observation light that have parallax, wherein, on condition that the single lens scope is connected to the camera head, the third optical path separation optics is detachably connected to the camera head.

15. The kit according to claim 11, further comprising a fourth optical path separation optics for use with the camera head and the single lens scope, wherein the fourth optical path separation optics includes a beam splitter which reflects a part of the observation light to generate the first observation light and transmits a part of the observation light to generate the second observation light.

* * * * *